US00PP10692P

United States Patent [19]

Mak-Leek

[11] Patent Number: Plant 10,692

[45] Date of Patent: Nov. 17, 1998

[54] ASIATIC HYBRID LILY PLANT NAMED 'PRIMA DONNA'

[76] Inventor: Ria Mak-Leek, 5595 Halls Ferry Rd., Independence, Oreg. 97351

[21] Appl. No.: 908,132

[22] Filed: Aug. 6, 1997

[51] Int. Cl.[6] ..... A01H 5/00

[52] U.S. Cl. ..... Plt./87.4

[58] Field of Search ..... Plt./87.4

[56] References Cited

U.S. PATENT DOCUMENTS

P.P. 9,023 12/1994 Hoff ..... Plt./87.4

P.P. 9,271 8/1995 Hoff ..... Plt./87.4

*Primary Examiner*—Howard J. Locker

[57] ABSTRACT

A new variety of hybrid lily plant bearing semi-upright flowers of excellent form and long persistence, both on the plant and as a cutflower. The flowers of the new plant are particularly characterized by their multiple coloration; yellow base, soft yellow and white center, and pink tips with dark spots at the base. This combination is completely new in the Asiatic hybrid divisions of lilies suited to forcing and to mas commercial cultivation. The variety shows tolerance against fusarium. The bulbs may be precooled and forced for cutflower production. The clone is vigorous and is a good grower and propagator.

1 Drawing Sheet

BACKGROUND OF THE INVENTION

My new variety of lily plant originated as a seedling which first flowered in 't Zand, Netherlands, in 1989. The breeding efforts had as their objective the production of multiple colored flowers, flowers oriented in an upright position, suited to forcing into flower out of season, heretofore unknown in the lily breeding art.

I achieved the desired objective by intercrossing selected upright yellow and white Asiatic seedlings with pink tips, suited to forcing for year-round use as cutflowers and carrying the recessive gene for multiple colors.

The flowers of my new lily are characterized by their multiple coloration, yellow base, soft yellow and white center, pink tips, and dark spots at the base of the flower, which surrounds a small dark brown ray extending from the nectary furrows. It possesses unusually strong, stout stems. In addition, the clone possesses to a high degree desirable characteristics of hybrid vigor. The clone is a good grower and propagator, as observed in Salem, Oreg.

My new variety of lily plant has been asexually reproduced by me and under my direction at my growing facilities in Salem, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, and in particular the novel and distinctive flower coloration with its yellow coloration at the bottom, soft pink cream at the center of the tepal and shading into a somewhat deep pink area at the edge with a few pigmented papillae and its flowers in upright position.

DESCRIPTION OF THE NEW VARIETY

The following is a detailed description of my new variety of Asiatic hybrid lily, with nomenclature according to the *International Lily Register (The Royal Horticultural Society of London, Second Edition,* 1969), and with color designations according to the Color Chart of The Royal Horticultural Society, published by the Society in 1966.

The Plant

Origin: Seedling.

*Seed parent.*—Selected unnamed soft yellow hybrid seedling.

*Pollen parent.*—Selected unnamed white with pink tips hybrid seedling.

Commercial classification: Hybrid Lilium clone.

Horticultural classification: Division 1-A, upright Asiatic hybrid lily, according to the Horticultural Classification of Lilies, The Royal Horticultural Society of London.

Form: Single stem, erect and stately.

Height: 45 to 75 cm from bulbs 14 to 18 cm in circumference, provided light levels are adequate; low light levels may cause "stretching."

Growth: Vigorous and upright.

Foliage quantity: Abundant.

Shape of leaf: Lanceolate (pointed).

Size of leaf: 15 to 25 mm wide×100 to 140 mm long.

Texture: Leathery and glossy.

Color: Pale green (R.H.S. CC 141A), lighter on lower side.

Bulb:

*Size.*—Any size, ranging to 25 cm circumference commercially.

*Color.*—White, with flushes of pink or yellow after exposure to light.

The Bud

Form: Obtuse, ovoid, and long.

Size 6 to 8 cm long and 6.5 to 7.5 cm in circumference just prior to opening.

Opening: Bud opens slowly, in response to morning light; this takes about one hour.

Color: Close to Orange White group R.H.S. CC 159A.

Tip of bud: Greyed Purple group R.H.S. CC 183B.

Color midrib: Close to Yellow Green group R.H.S. CC 144B.

Peduncle: Averages 5 to 10 cm, but it may elongate if light levels are too low or if bulbs have been improperly stored prior to forcing. Color is dark green with plum overlay.

The Flower

Blooming habit: Annually in midseason; flowers once and profusely.

Size: Flowers are medium large-sized, averaging 14.5 to 16.5 cm in diameter, the outer tepals are 2.5 to 3.5 cm wide, and the inner tepals are 4 to 5 cm wide.

Borne: In a single racemic inflorescence producing 10 to 14 flowers from a bulb 14 to 16 cm in circumference.

Shape: Flat the first day after opening and the second day slightly reflexing at the tips.

Tepalage: Typical of genus Lilium, with 6 imbricated tepals.

Tepal:

*Color*.—Soft cream pink with darker pink at the edge and yellowish marking at the base. Inner base of tepal: Yellow group R.H.S. CC 13B to 14B. Middle section of tepal: Yellow White group 158C to 159A. Tepal tip color: Red Purple group from R.H.S. CC 68D. Tepal spotting: The basal third of each tepal carries small magenta (R.H.S. CC Greyed Red group 178 A) spots.

*Longevity*.—Tepals stay on stems about two to three weeks.

Pedicel:

*Length*.—Average 5 to 8 cm long.

*Color*.—Yellow Green group R.H.S. CC 144A to 146A.

*Form*.—Sturdy and ascending, up to 45 degrees from the horizontal.

Color changes: Flower color may change because of changes in temperature and lighting as flower ages, as described under flower color.

Appearance: Flower is shiny.

Disease resistance: The flower and plant show resistance to disease; in particular, they are resistant to Fusarium bulb rot.

Fragrance: None.

Lasting quality: The flower is long lasting, both on the plant and as a cut-flower.

The Reproductive Organs

Stamens: Arrangement typical of genus Lilium. Six stamens with soft green to palest pink filaments 4.5 to 6 cm long.

Pollen and anthers (dehisced): Greyed Orange group R.H.S. CC 171B.

Pistil: One in number, 4 to 5.5 cm long.

Stigma: Greyed Red group R.H.S. CC 185C.

Characteristics of ovary: Characteristic of genus Lilium.

The Fruit

Fertility: The fruit bears fertile seed.

Shape: Ovoid.

Color at maturity: Soft brown, sometimes overlaid with soft plum.

I claim:

1. A new and distinctive variety of Asiatic hybrid lily plant substantially as herein shown and described, characterized by its high resistance to disease; its vigorous growth and rapid natural propagation; the excellence of its flower form, size, and substance; its versatility both as a garden plant and as a cut-flower producer from pre-cooled bulbs forced under glass out of season; and in particular by its unique multiple flower coloration; yellow base, soft yellow and white center, and pink tips with dark spots at the base.

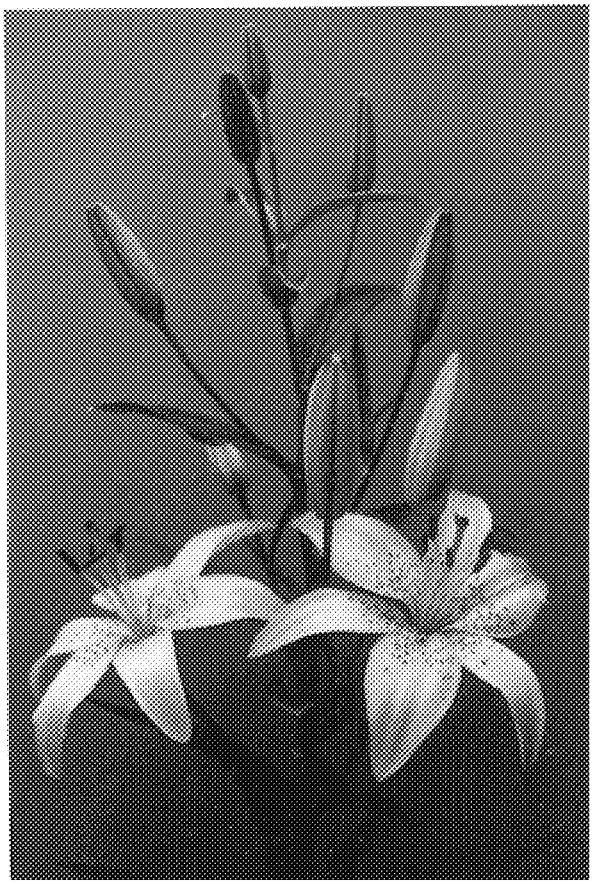

* * * * *